(12) United States Patent
Machamer

(10) Patent No.: US 12,042,180 B2
(45) Date of Patent: *Jul. 23, 2024

(54) FIXATORS FOR BONE STABILIZATION AND ASSOCIATED SYSTEMS AND METHODS

(71) Applicant: GLOBUS MEDICAL, INC., Audubon, PA (US)

(72) Inventor: David Machamer, Glen Mills, PA (US)

(73) Assignee: Globus Medical Inc., Audubon, PA (US)

( * ) Notice: Subject to any disclaimer, the term of this patent is extended or adjusted under 35 U.S.C. 154(b) by 333 days.

This patent is subject to a terminal disclaimer.

(21) Appl. No.: 17/676,304

(22) Filed: Feb. 21, 2022

(65) Prior Publication Data

US 2022/0175421 A1 Jun. 9, 2022

Related U.S. Application Data

(63) Continuation of application No. 16/411,388, filed on May 14, 2019, now Pat. No. 11,284,920, which is a continuation of application No. 15/708,193, filed on Sep. 19, 2017, now Pat. No. 10,327,815, which is a continuation of application No. 15/058,372, filed on Mar. 2, 2016, now Pat. No. 9,795,411.

(51) Int. Cl.
*A61B 17/62* (2006.01)

(52) U.S. Cl.
CPC .................................. *A61B 17/62* (2013.01)

(58) Field of Classification Search
CPC ..... A61B 17/54; A61B 17/62; A61B 17/6441; A61B 17/8861; A61B 17/848; A61B 17/06066; A61B 17/3205; A61B 17/06166; A61B 17/30; A61B 17/062; A61B 17/32; A61B 17/0467; A61B 17/1325; A61B 46/20; A61B 50/30; A61B 50/33; A61B 2017/00004; A61B 2017/320052; A61B 2017/305; A61B 2017/320044; A61B 2046/201; A61M 19/00; A61M 5/329; A61M 5/32; A61F 13/068; A61F 13/10; A61F 13/105; A61F 5/11

See application file for complete search history.

(56) References Cited

U.S. PATENT DOCUMENTS

| | | |
|---|---|---|
| 1,105,105 A | 7/1914 | Sherman |
| 2,486,303 A | 10/1949 | Longfellow |

(Continued)

FOREIGN PATENT DOCUMENTS

| | | |
|---|---|---|
| CN | 201987653 U | 9/2011 |
| CN | 202313691 U | 7/2012 |

(Continued)

*Primary Examiner* — Nicholas J Plionis

(57) ABSTRACT

The present technology relates generally to ring fixators and associated systems and methods. In some embodiments, for example, a ring fixator assembly comprises a ring configured to surround a fractured bone, a retention device disposed at a first position on the ring, and a tensioner clamp disposed at a second position on the ring. A wire extends between the retention device and the tensioner clamp. The tensioner clamp includes a first screw configured to secure the wire in position with respect to the tensioner clamp and a second screw configured to apply additional tension to the wire.

20 Claims, 7 Drawing Sheets

(56) References Cited

U.S. PATENT DOCUMENTS

| | | |
|---|---|---|
| 3,463,148 A | 8/1969 | Treace |
| 3,695,259 A | 10/1972 | Yost |
| 3,716,050 A | 2/1973 | Johnston |
| 3,976,061 A | 8/1976 | Volkov et al. |
| 4,219,015 A | 8/1980 | Steinemann |
| 4,493,317 A | 1/1985 | Klaue |
| 4,524,765 A | 6/1985 | de Zbikowski |
| 4,651,724 A | 3/1987 | Berentey et al. |
| 4,683,878 A | 8/1987 | Carter |
| 4,768,524 A | 9/1988 | Hardy |
| 4,781,183 A | 11/1988 | Casey et al. |
| 4,867,144 A | 9/1989 | Karas et al. |
| 4,923,471 A | 5/1990 | Morgan |
| 4,936,843 A * | 6/1990 | Sohngen ............ A61B 17/6441 606/56 |
| 4,966,599 A | 10/1990 | Pollock |
| 5,002,544 A | 3/1991 | Klaue et al. |
| 5,041,114 A | 8/1991 | Chapman et al. |
| 5,151,103 A | 9/1992 | Tepic et al. |
| 5,259,398 A | 11/1993 | Vrespa |
| 5,364,399 A | 11/1994 | Lowery et al. |
| 5,372,598 A | 12/1994 | Uhr et al. |
| 5,423,826 A | 6/1995 | Coates et al. |
| 5,468,242 A | 11/1995 | Reisberg |
| D365,634 S | 12/1995 | Morgan |
| 5,489,305 A | 2/1996 | Morgan |
| 5,527,311 A | 6/1996 | Procter et al. |
| 5,578,036 A | 11/1996 | Stone et al. |
| 5,601,553 A | 2/1997 | Trebing et al. |
| 5,676,667 A | 10/1997 | Hausman |
| 5,690,631 A | 11/1997 | Duncan et al. |
| 5,709,686 A | 1/1998 | Talos et al. |
| 5,709,687 A | 1/1998 | Pennig |
| 5,718,704 A | 2/1998 | Medoff |
| 5,718,705 A | 2/1998 | Sammarco |
| 5,728,095 A | 3/1998 | Taylor et al. |
| 5,746,741 A | 5/1998 | Kraus et al. |
| 5,746,742 A | 5/1998 | Runciman et al. |
| 5,766,175 A | 6/1998 | Martinotti |
| 5,766,176 A | 6/1998 | Duncan |
| 5,779,706 A | 7/1998 | Tschakaloff |
| 5,785,712 A | 7/1998 | Runciman et al. |
| 5,797,914 A | 8/1998 | Leibinger |
| 5,814,048 A | 9/1998 | Morgan |
| 5,925,048 A | 7/1999 | Ahmad et al. |
| 5,928,230 A | 7/1999 | Tosic |
| 5,938,664 A | 8/1999 | Winquist et al. |
| 5,961,519 A | 10/1999 | Bruce et al. |
| 5,980,540 A | 11/1999 | Bruce |
| 6,001,099 A | 12/1999 | Huebner |
| 6,071,291 A | 6/2000 | Forst et al. |
| 6,093,201 A | 7/2000 | Cooper et al. |
| 6,096,040 A | 8/2000 | Esser |
| 6,107,718 A | 8/2000 | Schustek et al. |
| 6,152,927 A | 11/2000 | Farris et al. |
| 6,206,881 B1 | 3/2001 | Frigg et al. |
| 6,283,969 B1 | 9/2001 | Grusin et al. |
| 6,309,393 B1 | 10/2001 | Tepic et al. |
| 6,322,562 B1 | 11/2001 | Wolter |
| 6,364,882 B1 | 4/2002 | Orbay |
| D458,683 S | 6/2002 | Bryant et al. |
| D458,684 S | 6/2002 | Bryant et al. |
| 6,533,786 B1 | 3/2003 | Needham et al. |
| D479,331 S | 9/2003 | Pike et al. |
| 6,623,486 B1 | 9/2003 | Weaver et al. |
| 6,669,700 B1 | 12/2003 | Farris et al. |
| 6,669,701 B2 | 12/2003 | Steiner et al. |
| 6,712,820 B2 | 3/2004 | Orbay |
| 6,719,759 B2 | 4/2004 | Wagner et al. |
| 6,730,091 B1 | 5/2004 | Pfefferle et al. |
| 6,866,665 B2 | 3/2005 | Orbay |
| 6,955,677 B2 | 10/2005 | Dahners |
| 6,974,461 B1 | 12/2005 | Wolter |
| 7,001,387 B2 | 2/2006 | Farris et al. |
| 7,063,701 B2 | 6/2006 | Michelson |
| 7,090,676 B2 | 8/2006 | Huebner et al. |
| 7,128,744 B2 | 10/2006 | Weaver et al. |
| 7,137,987 B2 | 11/2006 | Patterson et al. |
| 7,153,309 B2 | 12/2006 | Huebner et al. |
| 7,179,260 B2 | 2/2007 | Gerlach et al. |
| 7,250,053 B2 | 7/2007 | Orbay |
| 7,294,130 B2 | 11/2007 | Orbay |
| 7,322,983 B2 | 1/2008 | Harris |
| 7,341,589 B2 | 3/2008 | Weaver et al. |
| 7,344,538 B2 | 3/2008 | Myerson et al. |
| 7,354,441 B2 | 4/2008 | Frigg |
| 7,604,657 B2 | 10/2009 | Orbay et al. |
| 7,632,277 B2 | 12/2009 | Woll et al. |
| 7,635,381 B2 | 12/2009 | Orbay |
| 7,637,928 B2 | 12/2009 | Fernandez |
| 7,655,029 B2 | 2/2010 | Niedernberger et al. |
| 7,655,047 B2 | 2/2010 | Swords |
| 7,695,472 B2 | 4/2010 | Young |
| 7,717,946 B2 | 5/2010 | Oepen et al. |
| 7,722,653 B2 | 5/2010 | Young et al. |
| 7,740,648 B2 | 6/2010 | Young et al. |
| D622,853 S | 8/2010 | Raven, III |
| 7,771,457 B2 | 8/2010 | Kay et al. |
| 7,776,076 B2 | 8/2010 | Grady, Jr. et al. |
| 7,857,838 B2 | 12/2010 | Orbay |
| 7,867,260 B2 | 1/2011 | Meyer et al. |
| 7,867,261 B2 | 1/2011 | Sixto, Jr. et al. |
| 7,875,062 B2 | 1/2011 | Lindemann et al. |
| 7,905,910 B2 | 3/2011 | Gerlach et al. |
| 7,909,858 B2 | 3/2011 | Gerlach et al. |
| 7,951,178 B2 | 5/2011 | Jensen |
| 7,951,179 B2 | 5/2011 | Matityahu |
| 7,976,570 B2 | 7/2011 | Wagner et al. |
| D643,121 S | 8/2011 | Millford et al. |
| D646,785 S | 10/2011 | Milford |
| 8,043,297 B2 | 10/2011 | Grady, Jr. et al. |
| 8,057,520 B2 | 11/2011 | Ducharme et al. |
| 8,062,296 B2 | 11/2011 | Orbay et al. |
| 8,100,953 B2 | 1/2012 | White et al. |
| 8,105,367 B2 | 1/2012 | Austin et al. |
| 8,114,081 B2 | 2/2012 | Kohut et al. |
| 8,118,846 B2 | 2/2012 | Leither et al. |
| 8,118,848 B2 | 2/2012 | Ducharme et al. |
| 8,162,950 B2 | 4/2012 | Digeser et al. |
| 8,167,918 B2 | 5/2012 | Strnad et al. |
| 8,177,820 B2 | 5/2012 | Anapliotis et al. |
| 8,246,661 B2 | 8/2012 | Beutter et al. |
| 8,252,032 B2 | 8/2012 | White et al. |
| 8,257,403 B2 | 9/2012 | Den Hartog et al. |
| 8,257,405 B2 | 9/2012 | Haidukewych et al. |
| 8,257,406 B2 | 9/2012 | Kay et al. |
| 8,262,707 B2 | 9/2012 | Huebner et al. |
| 8,267,972 B1 | 9/2012 | Gehlert |
| 8,317,842 B2 | 11/2012 | Graham et al. |
| 8,323,321 B2 | 12/2012 | Gradl |
| 8,337,535 B2 | 12/2012 | White et al. |
| 8,343,155 B2 | 1/2013 | Fisher et al. |
| 8,382,807 B2 | 2/2013 | Austin et al. |
| 8,394,098 B2 | 3/2013 | Orbay et al. |
| 8,394,130 B2 | 3/2013 | Orbay et al. |
| 8,398,685 B2 | 3/2013 | McGarity et al. |
| 8,403,966 B2 | 3/2013 | Ralph et al. |
| 8,419,775 B2 | 4/2013 | Orbay et al. |
| 8,435,272 B2 | 5/2013 | Dougherty et al. |
| 8,439,918 B2 | 5/2013 | Gelfand |
| 8,444,679 B2 | 5/2013 | Ralph et al. |
| 8,491,593 B2 | 7/2013 | Prien et al. |
| 8,506,608 B2 | 8/2013 | Cerynik et al. |
| 8,512,384 B2 | 8/2013 | Beutter et al. |
| 8,512,385 B2 | 8/2013 | White et al. |
| 8,518,090 B2 | 8/2013 | Huebner et al. |
| 8,523,862 B2 | 9/2013 | Murashko, Jr. |
| 8,523,919 B2 | 9/2013 | Huebner et al. |
| 8,523,921 B2 | 9/2013 | Horan et al. |
| 8,540,755 B2 | 9/2013 | Whitmore |
| 8,551,095 B2 | 10/2013 | Fritzinger et al. |
| 8,551,143 B2 | 10/2013 | Norris et al. |
| 8,568,462 B2 | 10/2013 | Sixto, Jr. et al. |
| 8,574,268 B2 | 11/2013 | Chan et al. |

(56) References Cited

U.S. PATENT DOCUMENTS

| | | |
|---|---|---|
| 8,597,334 B2 | 12/2013 | Mocanu |
| 8,603,147 B2 | 12/2013 | Sixto, Jr. et al. |
| 8,617,224 B2 | 12/2013 | Kozak et al. |
| 8,632,574 B2 | 1/2014 | Kortenbach et al. |
| 8,641,741 B2 | 2/2014 | Murashko, Jr. |
| 8,641,744 B2 | 2/2014 | Weaver et al. |
| 8,663,224 B2 | 3/2014 | Overes et al. |
| 8,728,082 B2 | 5/2014 | Fritzinger et al. |
| 8,728,126 B2 | 5/2014 | Steffen |
| 8,740,905 B2 | 6/2014 | Price et al. |
| 8,747,442 B2 | 6/2014 | Orbay et al. |
| 8,764,751 B2 | 7/2014 | Orbay et al. |
| 8,764,808 B2 | 7/2014 | Gonzalez-Hernandez |
| 8,777,998 B2 | 7/2014 | Daniels et al. |
| 8,790,376 B2 | 7/2014 | Fritzinger et al. |
| 8,790,377 B2 | 7/2014 | Ralph et al. |
| 8,808,333 B2 | 8/2014 | Kuster et al. |
| 8,808,334 B2 | 8/2014 | Strnad et al. |
| 8,834,532 B2 | 9/2014 | Velikov et al. |
| 8,834,537 B2 | 9/2014 | Castanada et al. |
| 8,852,246 B2 | 10/2014 | Hansson |
| 8,852,249 B2 | 10/2014 | Ahrens et al. |
| 8,858,555 B2 | 10/2014 | Crozet et al. |
| 8,864,802 B2 | 10/2014 | Schwager et al. |
| 8,870,931 B2 | 10/2014 | Dahners et al. |
| 8,888,825 B2 | 11/2014 | Batsch et al. |
| 8,906,076 B2 | 12/2014 | Mocanu et al. |
| 8,911,482 B2 | 12/2014 | Lee et al. |
| 8,926,675 B2 | 1/2015 | Leung et al. |
| 8,940,026 B2 | 1/2015 | Hilse et al. |
| 8,940,028 B2 | 1/2015 | Austin et al. |
| 8,940,029 B2 | 1/2015 | Leung et al. |
| 8,945,128 B2 | 2/2015 | Singh et al. |
| 8,951,252 B2 | 2/2015 | Steiner et al. |
| 8,951,291 B2 | 2/2015 | Impellizzeri |
| 8,968,368 B2 | 3/2015 | Tepic |
| 9,011,457 B2 | 4/2015 | Grady, Jr. et al. |
| 9,023,052 B2 | 5/2015 | Lietz et al. |
| 9,050,151 B2 | 6/2015 | Schilter |
| 9,072,555 B2 | 7/2015 | Michel |
| 9,072,557 B2 | 7/2015 | Fierlbeck et al. |
| 9,107,678 B2 | 8/2015 | Murner et al. |
| 9,107,711 B2 | 8/2015 | Hainard |
| 9,107,713 B2 | 8/2015 | Horan et al. |
| 9,107,718 B2 | 8/2015 | Isch |
| 9,113,970 B2 | 8/2015 | Lewis et al. |
| 9,149,310 B2 | 10/2015 | Fritzinger et al. |
| 9,161,791 B2 | 10/2015 | Frigg |
| 9,161,795 B2 | 10/2015 | Chasbrummel et al. |
| 9,168,075 B2 | 10/2015 | Dell'Oca |
| 9,179,950 B2 | 11/2015 | Zajac et al. |
| 9,179,956 B2 | 11/2015 | Cerynik et al. |
| 9,180,020 B2 | 11/2015 | Gause et al. |
| 9,211,151 B2 | 12/2015 | Weaver et al. |
| 9,259,217 B2 | 2/2016 | Fritzinger et al. |
| 9,259,255 B2 | 2/2016 | Lewis et al. |
| 9,271,769 B2 | 3/2016 | Batsch et al. |
| 9,283,010 B2 | 3/2016 | Medoff et al. |
| 9,295,506 B2 | 3/2016 | Raven, III et al. |
| 9,314,284 B2 | 4/2016 | Chan et al. |
| 9,320,554 B2 | 4/2016 | Greenberg et al. |
| 9,322,562 B2 | 4/2016 | Takayama et al. |
| 9,370,388 B2 | 6/2016 | Globerman et al. |
| D765,851 S | 9/2016 | Early et al. |
| 9,433,407 B2 | 9/2016 | Fritzinger et al. |
| 9,433,452 B2 | 9/2016 | Weiner et al. |
| 9,468,479 B2 | 10/2016 | Marotta et al. |
| 9,480,512 B2 | 11/2016 | Orbay |
| 9,486,262 B2 | 11/2016 | Andermahr et al. |
| 9,492,213 B2 | 11/2016 | Orbay |
| 9,510,878 B2 | 12/2016 | Nanavati et al. |
| 9,510,880 B2 | 12/2016 | Terrill et al. |
| 9,526,543 B2 | 12/2016 | Castaneda et al. |
| 9,545,277 B2 | 1/2017 | Wolf et al. |
| 9,549,819 B1 | 1/2017 | Bravo et al. |
| 9,566,097 B2 | 2/2017 | Fierlbeck et al. |
| 9,579,133 B2 | 2/2017 | Guthlein |
| 9,622,799 B2 | 4/2017 | Orbay et al. |
| 9,636,157 B2 | 5/2017 | Medoff |
| 9,649,141 B2 | 5/2017 | Raven, III et al. |
| 9,668,794 B2 | 6/2017 | Kuster et al. |
| 9,801,670 B2 | 10/2017 | Hashmi et al. |
| 9,814,504 B2 | 11/2017 | Ducharme et al. |
| 2002/0045901 A1 | 4/2002 | Wagner et al. |
| 2004/0097937 A1 | 5/2004 | Pike et al. |
| 2005/0107796 A1 | 5/2005 | Gerlach et al. |
| 2005/0131413 A1 | 6/2005 | O'Driscoll et al. |
| 2005/0187551 A1 | 8/2005 | Orbay et al. |
| 2006/0149265 A1 | 7/2006 | James et al. |
| 2006/0241607 A1 | 10/2006 | Myerson et al. |
| 2006/0276786 A1 | 12/2006 | Brinker |
| 2007/0173840 A1 | 7/2007 | Huebner |
| 2007/0270849 A1 | 11/2007 | Orbay et al. |
| 2007/0288022 A1 | 12/2007 | Lutz |
| 2008/0021477 A1 | 1/2008 | Strnad et al. |
| 2008/0234749 A1 | 9/2008 | Forstein |
| 2008/0275510 A1 | 11/2008 | Schonhardt et al. |
| 2009/0024172 A1 | 1/2009 | Pizzicara |
| 2009/0024173 A1 | 1/2009 | Reis, Jr. |
| 2009/0118773 A1 | 5/2009 | James et al. |
| 2009/0198285 A1 | 8/2009 | Raven, III |
| 2009/0228010 A1 | 9/2009 | Gonzalez-Hernandez et al. |
| 2009/0228047 A1 | 9/2009 | Derouet et al. |
| 2009/0248084 A1 | 10/2009 | Hintermann |
| 2009/0281543 A1 | 11/2009 | Orbay et al. |
| 2009/0299369 A1 | 12/2009 | Orbay et al. |
| 2009/0312760 A1 | 12/2009 | Forstein et al. |
| 2010/0057086 A1 | 3/2010 | Price et al. |
| 2010/0114097 A1 | 5/2010 | Siravo et al. |
| 2010/0121326 A1 | 5/2010 | Woll et al. |
| 2010/0274247 A1 | 10/2010 | Grady, Jr. et al. |
| 2011/0106086 A1 | 5/2011 | Laird |
| 2011/0218580 A1 | 9/2011 | Schwager et al. |
| 2012/0010667 A1 | 1/2012 | Eglseder |
| 2012/0059424 A1 | 3/2012 | Epperly et al. |
| 2012/0203227 A1 | 8/2012 | Martin |
| 2012/0232599 A1 | 9/2012 | Schoenly et al. |
| 2012/0323284 A1 | 12/2012 | Baker et al. |
| 2013/0018426 A1 | 1/2013 | Tsai et al. |
| 2013/0046347 A1 | 2/2013 | Cheng et al. |
| 2013/0060291 A1 | 3/2013 | Petersheim |
| 2013/0123841 A1 | 5/2013 | Lyon |
| 2013/0138156 A1 | 5/2013 | Derouet |
| 2013/0150902 A1 | 6/2013 | Leite |
| 2013/0165981 A1 | 6/2013 | Clasbrummet et al. |
| 2013/0211463 A1 | 8/2013 | Mizuno et al. |
| 2013/0289630 A1 | 10/2013 | Fritzinger |
| 2014/0005728 A1 | 1/2014 | Koay et al. |
| 2014/0018862 A1 | 1/2014 | Koay et al. |
| 2014/0031879 A1 | 1/2014 | Sixto, Jr. et al. |
| 2014/0066998 A1 | 3/2014 | Martin |
| 2014/0094856 A1 | 4/2014 | Sinha |
| 2014/0121710 A1 | 5/2014 | Weaver et al. |
| 2014/0180345 A1 | 6/2014 | Chan et al. |
| 2014/0277178 A1 | 9/2014 | O'Kane et al. |
| 2014/0277181 A1 | 9/2014 | Garlock |
| 2014/0316473 A1 | 10/2014 | Pfeffer et al. |
| 2014/0330320 A1 | 11/2014 | Wolter |
| 2014/0378975 A1 | 12/2014 | Castaneda et al. |
| 2015/0051650 A1 | 2/2015 | Verstreken et al. |
| 2015/0051651 A1 | 2/2015 | Terrill et al. |
| 2015/0073486 A1 | 3/2015 | Marotta et al. |
| 2015/0105829 A1 | 4/2015 | Laird |
| 2015/0112355 A1 | 4/2015 | Dahners et al. |
| 2015/0134011 A1 | 5/2015 | Medoff |
| 2015/0142065 A1 | 5/2015 | Schonhardt et al. |
| 2015/0190185 A1 | 7/2015 | Koay et al. |
| 2015/0209091 A1 | 7/2015 | Sixto, Jr. et al. |
| 2015/0216571 A1 | 8/2015 | Impellizzeri |
| 2015/0223852 A1 | 8/2015 | Lietz et al. |
| 2015/0272638 A1 | 10/2015 | Langford |
| 2015/0282851 A1 | 10/2015 | Michel |
| 2015/0313653 A1 | 11/2015 | Ponce et al. |
| 2015/0313654 A1 | 11/2015 | Horan et al. |

(56) References Cited

U.S. PATENT DOCUMENTS

| | | |
|---|---|---|
| 2015/0327898 A1 | 11/2015 | Martin |
| 2015/0351816 A1 | 12/2015 | Lewis et al. |
| 2015/0374421 A1 | 12/2015 | Rocci et al. |
| 2016/0022336 A1 | 1/2016 | Bateman |
| 2016/0030035 A1 | 2/2016 | Zajac et al. |
| 2016/0045237 A1 | 2/2016 | Cerynik et al. |
| 2016/0045238 A1 | 2/2016 | Bohay et al. |
| 2016/0074081 A1 | 3/2016 | Weaver et al. |
| 2016/0166297 A1 | 6/2016 | Mighell et al. |
| 2016/0166298 A1 | 6/2016 | Mighell et al. |
| 2016/0183990 A1 | 6/2016 | Koizumi et al. |
| 2016/0262814 A1 | 9/2016 | Wainscott |
| 2016/0278828 A1 | 9/2016 | Ragghianti |
| 2016/0310183 A1 | 10/2016 | Shah et al. |
| 2016/0310185 A1 | 10/2016 | Sixto et al. |
| 2016/0324552 A1 | 11/2016 | Baker et al. |
| 2016/0354122 A1 | 12/2016 | Montello et al. |
| 2017/0035478 A1 | 2/2017 | Andermahr et al. |
| 2017/0042592 A1 | 2/2017 | Kim |
| 2017/0042596 A9 | 2/2017 | Mighell et al. |
| 2017/0049493 A1 | 2/2017 | Gauneau et al. |
| 2017/0065312 A1 | 3/2017 | Lauf et al. |
| 2017/0105775 A1 | 4/2017 | Ricker et al. |
| 2017/0215931 A1 | 8/2017 | Cremer et al. |

FOREIGN PATENT DOCUMENTS

| | | |
|---|---|---|
| CN | 202821574 U | 3/2013 |
| CN | 202821575 U | 3/2013 |
| CN | 203506858 U | 4/2014 |
| CN | 203815563 U | 9/2014 |
| CN | 105982727 A | 10/2016 |
| EP | 3213703 A2 | 9/2017 |
| FR | 2279371 | 2/1976 |
| FR | 2595045 | 2/1986 |
| FR | 2846870 A1 | 5/2004 |
| FR | 2928259 A1 | 9/2009 |
| JP | 62-253046 A | 11/1987 |
| JP | 2003210478 A | 7/2003 |
| JP | 2004344365 A | 12/2004 |
| TW | 201316942 A | 5/2013 |
| WO | 8701625 | 10/1987 |
| WO | 2014055202 A1 | 4/2014 |
| WO | 2015137976 A1 | 9/2015 |
| WO | 2016079504 A1 | 5/2016 |

\* cited by examiner

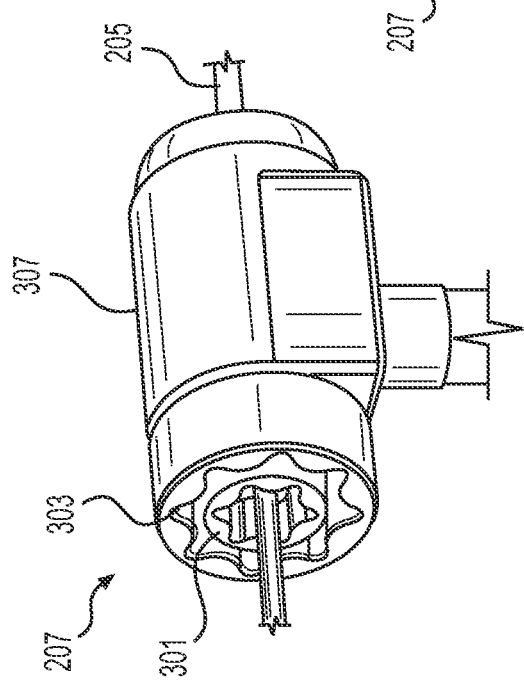
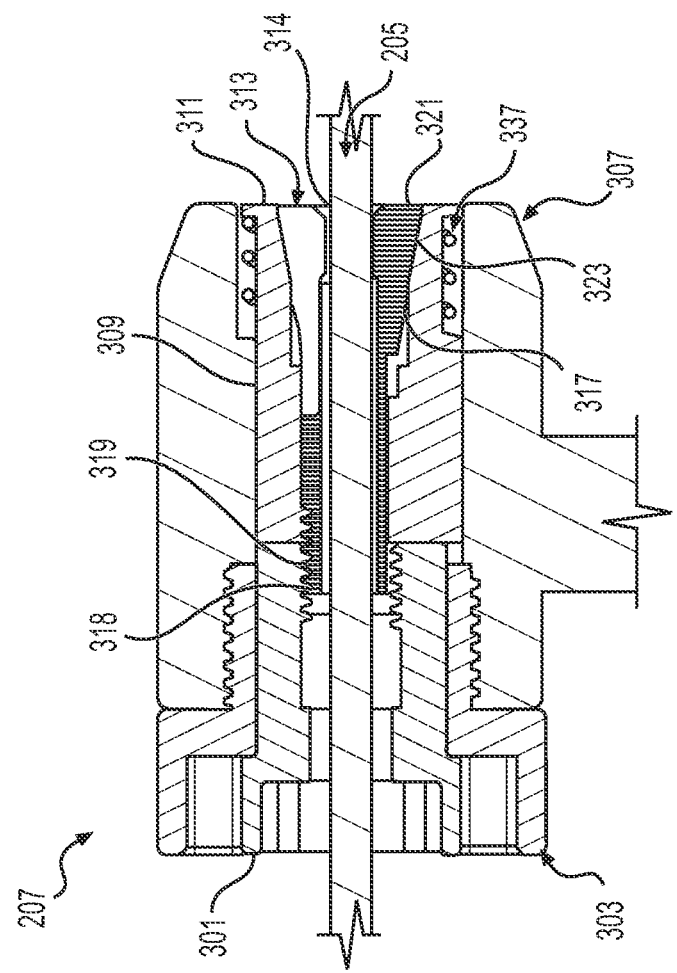

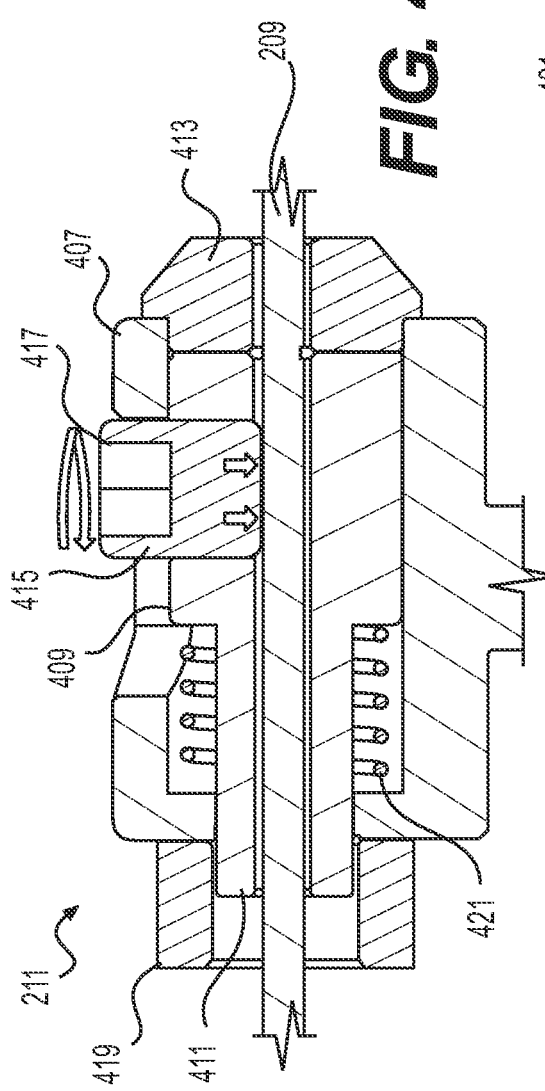
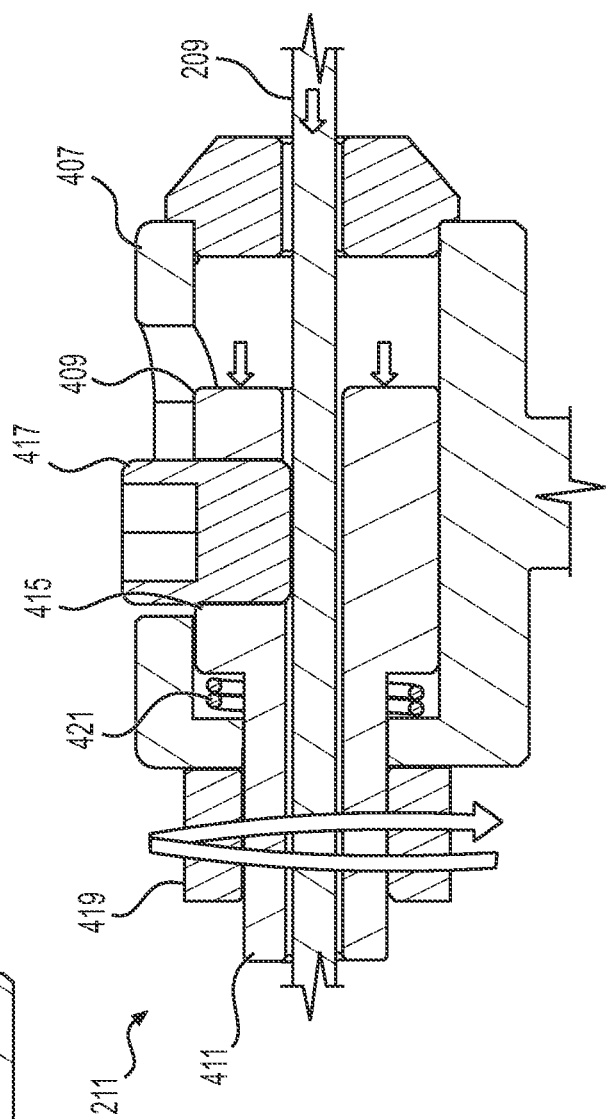

FIXATORS FOR BONE STABILIZATION AND ASSOCIATED SYSTEMS AND METHODS

CROSS REFERENCE TO RELATED APPLICATIONS

This application is a continuation application of U.S. patent application Ser. No. 16/411,388 filed on May 14, 2019, which is a continuation application of U.S. patent application Ser. No. 15/708,193, filed on Sep. 19, 2017 (published as U.S. Pat. Pub. No. 2018-0000519), which is a continuation application of U.S. patent application Ser. No. 15/058,372, filed Mar. 2, 2016 (now U.S. Pat. No. 9,795,411). The disclosures referenced above are being incorporated herein by reference in their entirety.

TECHNICAL FIELD

The present technology is generally related to fixators for stabilization of fractured bones.

BACKGROUND

For background purposes, a ring fixator is a stabilization device that is used on patients to treat complex and/or open bone fractures. The ring fixator is comprised of pins and wires secured to external scaffolding to provide support to a limb. This allows a bone or joint to be stabilized (e.g., via fusion) during trauma or limb reconstruction.

A ring fixator can be formed by a plurality of rings that are fixed to bone via tensioned pins or wires. The ring fixator can be used, for example, in fractured areas of high severity (e.g., with gunshot wounds), whereby traditional fixators are incapable of stabilizing the tissue. The ring fixators can remain in place until bone or joint stabilization is complete, upon which they can be removed.

SUMMARY

In one aspect of the present invention, a ring fixator assembly is disclosed. The ring fixator assembly includes a ring configured to surround a bone, a retention device disposed at a first position on the ring, a tensioner clamp disposed at a second position on the ring, and a wire extending between the retention device and the tensioner clamp. The tensioner clamp includes a clamping member configured to secure the wire in position with respect to the tensioner clamp and a tensioning member configured to apply tension to the wire.

In another aspect of the present invention, a tensioner clamp for a ring fixator assembly is disclosed. The tensioner clamp includes a central passage configured to receive a wire therein, a clamping member configured to secure the wire in position within the central passage, and a tensioning member configured to apply tension to the wire after the clamping member has secured the wire in position.

BRIEF DESCRIPTION OF THE DRAWINGS

FIGS. 3A-3D illustrate various views of the first tensioner clamp configured in accordance with an embodiment of the present technology.

FIGS. 4A-4C illustrate various views of the second tensioner clamp configured in accordance with an embodiment of the present technology.

DETAILED DESCRIPTION

Figure 1:
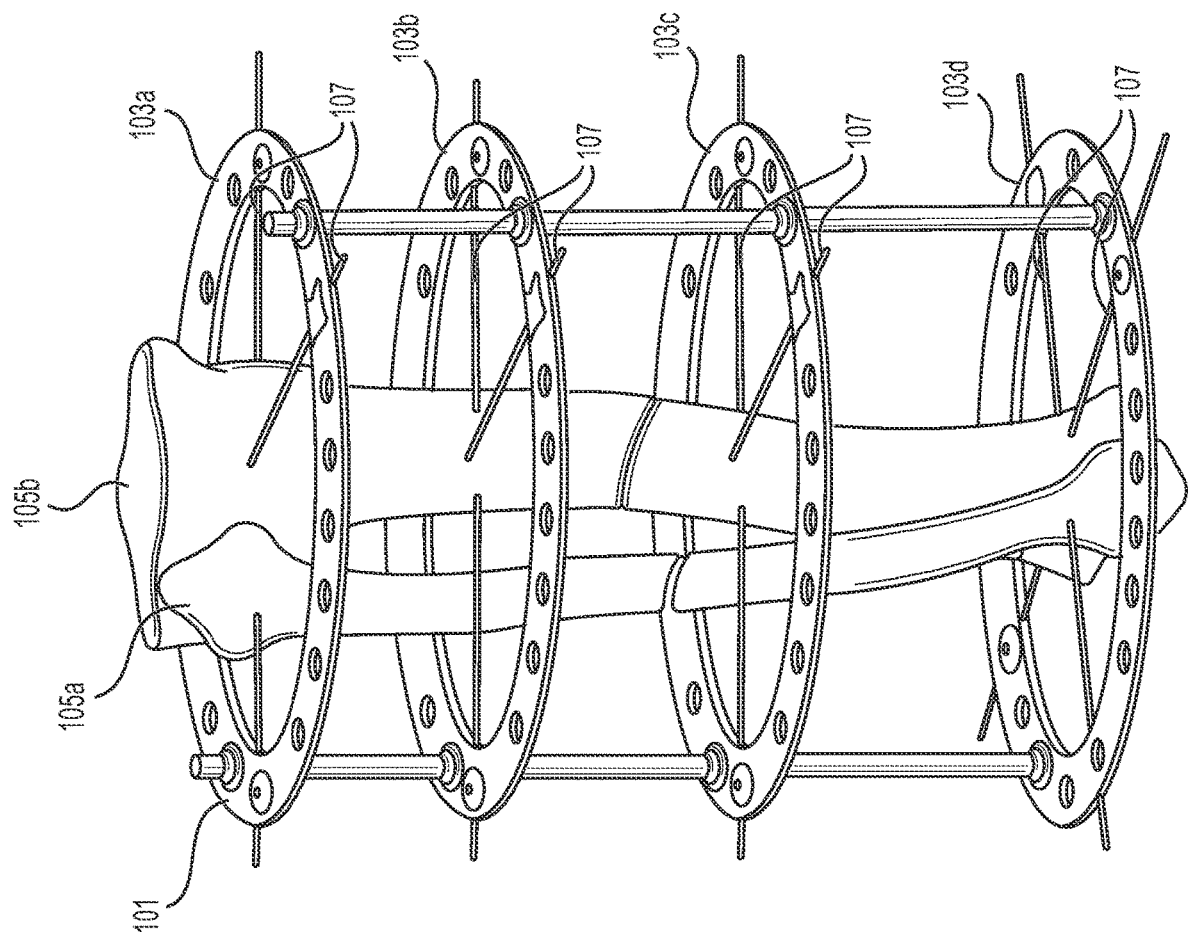
FIG. 1 is a schematic illustration of a ring fixator assembly.

The present disclosure relates to improved ring fixators. An example of a ring fixator is shown in FIG. 1. The ring fixator 101 includes multiple rings 103*a-d* that surround a patient's fractured bones 105*a*, 105*b*. A plurality of wires 107 extend across the individual rings 103*a-d*, passing through the bones 105*a*, 105*b*, thereby providing stability to the fractured bones 105*a*, 105*b* while the fractured bones are healed (e.g., via fusion). The ring fixator 101 can be positioned on the patient for as long as necessary until stabilization (e.g., via fusion) is achieved.

As shown in FIG. 1, each of the rings 103*a-d* of the ring fixator 101 can include one or more wires 107 that are attached to a ring member. To attach the one or more wires 107 to their respective ring member 103*a-d*, each of the wires would first be clamped to the ring member (e.g., via a clamping instrument). Following attachment, the one or more wires 107 would then be placed in tension (e.g., via a tensioner). These steps would involve two instruments— namely the clamping instrument for attachment and the tensioner for tensioning. The use of two instruments to perform multiple steps can be time consuming in an operation room, as a surgeon would have to first seek out a clamping instrument and then a tensioner for each location on the ring wherein a wire is attached.

Figure 2:
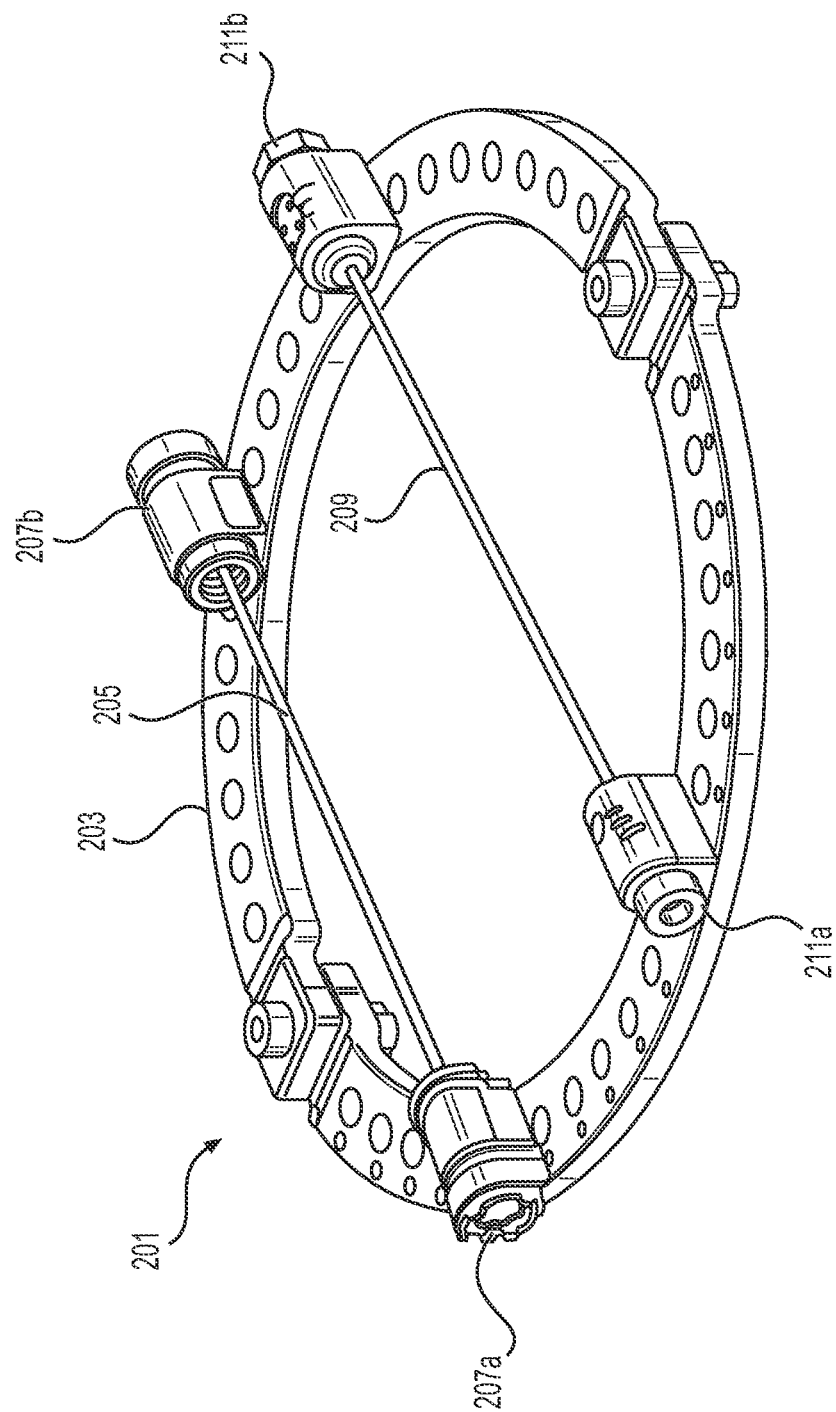
FIG. 2 illustrates a ring fixator including first and second tensioner clamps in accordance with an embodiment of the present technology.

The present disclosure is related to embodiments of an improved ring fixator utilizing a combined clamp and tensioner ("tensioner clamp"), which reduces a need to have both a clamping instrument and a separate tensioning instrument. Advantageously, in some embodiments, a single instrument can be used with the tensioner clamp, thereby saving valuable time in an operating room. FIGS. 2-6 show different embodiments of an improved tensioner clamp in accordance with some embodiments. In particular, as shown in FIG. 2, a ring fixator assembly 201 can utilize one or more types of tensioner clamps. One type of tensioner clamp 207*a*, 207*b* is shown attached to wire 205, while a second type of tensioner clamp 211*a*, 211*b* is shown attached to wire 209.

FIG. 2 illustrates a ring 203 of a ring fixator assembly 201 ("ring fixator 201") having four tensioner clamps affixed around the perimeter of the ring 203. A first wire 205 extends between two of a first type of tensioner clamp 207*a*, 207*b*, while a second wire 209 extends between two of a second type of tensioner clamp 211*a*, 211*b*. Each of the tensioner clamps 207 and 211 are configured to both clamp the wires 205 and 209 in place and to apply tension to the wires 205 and 209 after they have been clamped. In some embodiments, a single instrument can be used for both clamping and tensioning, thereby eliminating the need for multiple instruments.

Figure 3C:
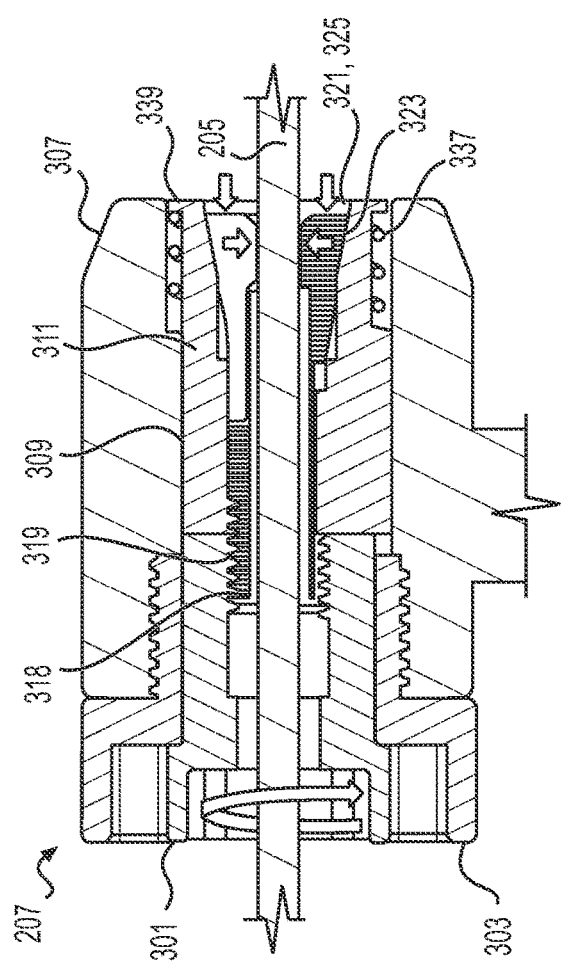

The first and second tensioner clamps 207 and 211 are described in more detail below. Although the embodiment illustrated in FIG. 2 includes first and second tensioner clamps 207 and 211, in other embodiments the ring fixator may include only one type of tensioner clamp. In addition, in some embodiments the wire can be secured at one end by a simple retention device (e.g., a clamp device that cannot apply additional tension), while the wire is secured at the other end by a tensioner clamp. In additional embodiments, the term retention clamp can apply not only to a clamp that cannot apply additional tension, but also to a tensioner clamp. A first tensioner clamp 207 is shown in FIGS. 3A-3D, while a second tensioner clamp 211 is shown in FIGS. 4A-4C. FIG. 3A is a perspective view of a first tensioner clamp 207 engaging the wire 205 in accordance with some embodiments. As illustrated, the first tensioner clamp 207 includes a clamping screw 301 coaxial with a tensioning screw 303. A first driver (not shown) can be used to rotate the clamping screw 301, which causes a clamping member to secure the inner wire 205. A second driver (not shown) can then be used to rotate the tensioning screw 303, which causes tension to be applied to the inner wire 205. In other embodiments, a single driver can be used to control both the clamping screw 301 and the tensioning screw 303, thereby reducing the need for two separate drivers. In other embodiments, a single instrument can house a first driver for operating the clamping screw 301 and a second driver for operating the tensioning screw 303, thereby advantageously allowing a single instrument to perform both clamping and tensioning.

Figure 3D:
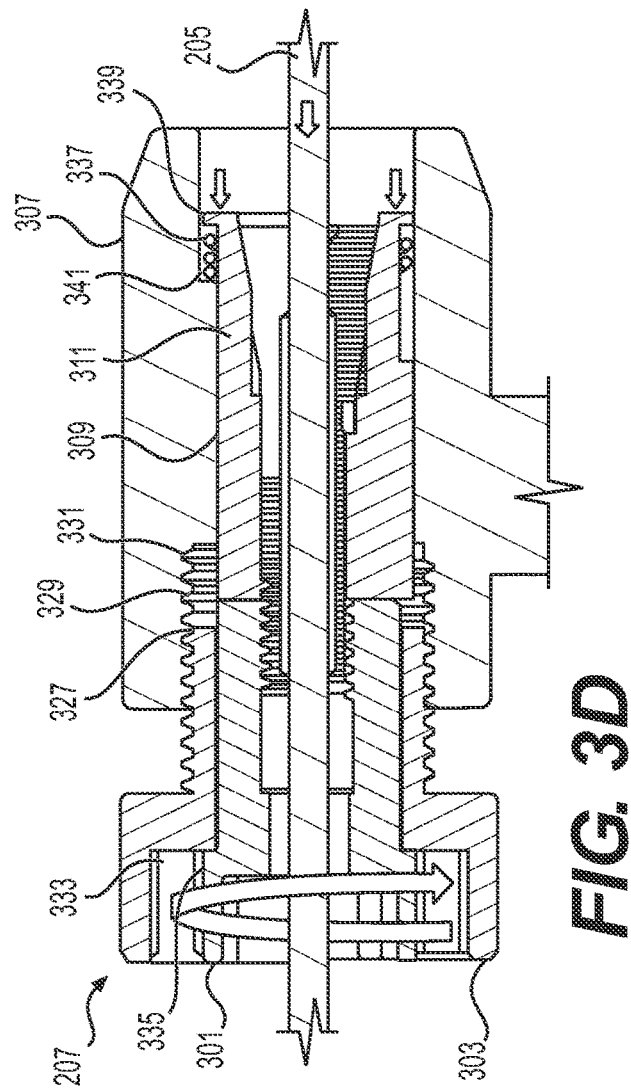
Figure 4A:
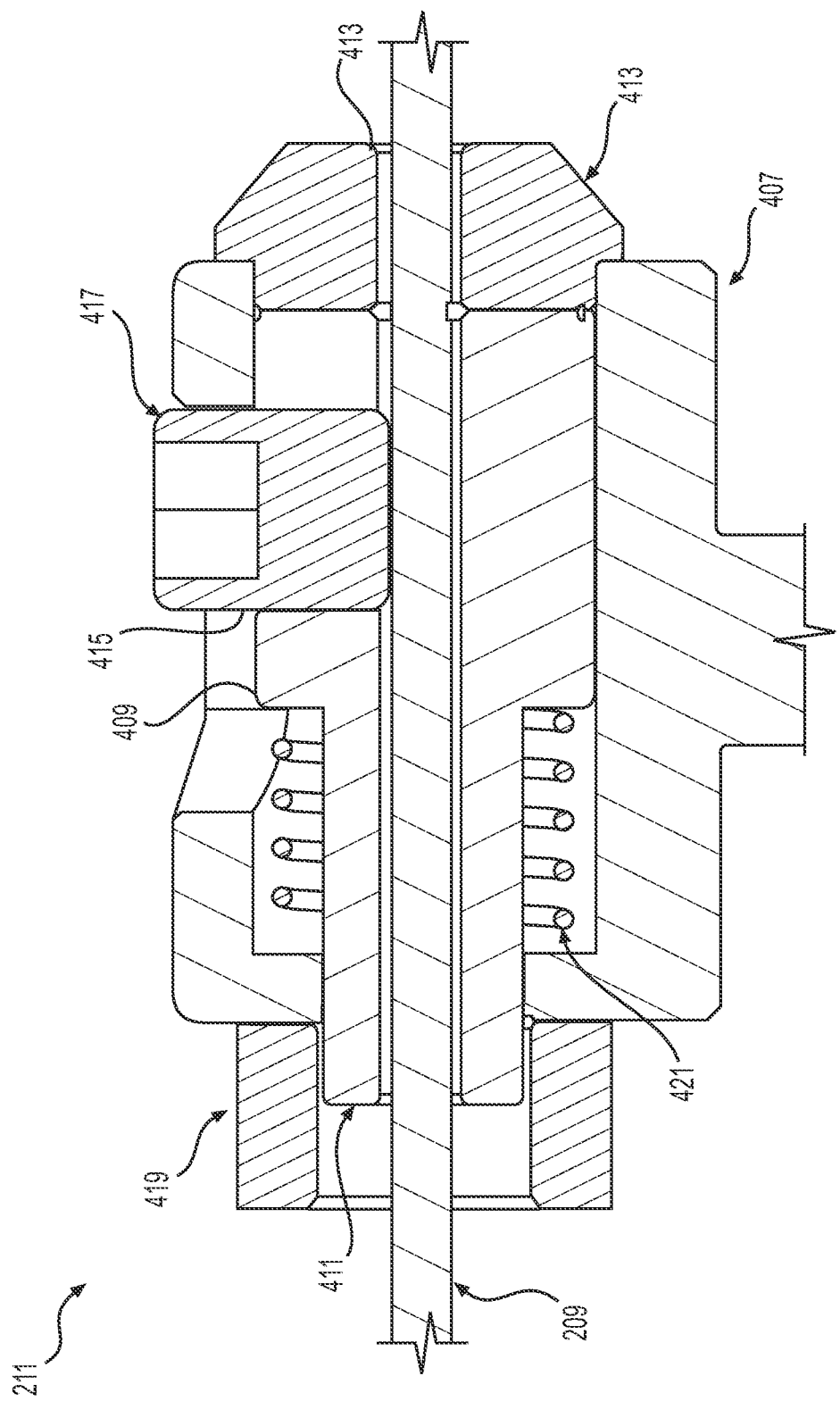

FIGS. 3B-3D illustrate side cross-sectional views of the first tensioner clamp 207 engaged with the wire 205 during different points of operation of the first tensioner clamp 207. In particular, FIG. 3B illustrates the first tensioner clamp 207 prior to clamping the wire 205, FIG. 3C illustrates the first tensioner clamp 207 after clamping the wire 205, and FIG. 3D illustrates the first tensioner clamp 207 after both clamping and tensioning the wire 205.

Referring to FIG. 3B, the first tensioner clamp 207 includes an outer housing 307. The housing 307 can be configured to be fixedly attached to a ring of a ring fixator. Within the housing 307 is a clamping assembly 309 which clamps the wire 205 in place in response to rotation of the clamping screw 301. The clamping assembly 309 includes a collet housing 311 received within the outer housing 307 and a collet 313 received within the collet housing 311. The collet 313 has a central opening 314 to receive the wire 205 therein, and includes a proximal end portion 315 and a distal end portion 317 opposite to the proximal end portion 315. The proximal end portion 315 includes threads 318 that are configured to engage with corresponding threads 319 of the clamping screw 301. The distal end portion 317 includes a compressible member 321 that engages with an angled surface 323 of the collet housing 311.

As illustrated in FIG. 3C, during operation, the clamping screw 301 is rotated, causing the collet 313 to be retracted relative to the collet housing 311. During this retraction, the compressible member 321 of the collet 313 engages with the angled surface 323 of the collet housing 311, thereby causing the compressible member 321 to press inwardly onto the wire 205, effectively clamping the wire 205 in place. In the illustrated embodiment, the compressible member 321 takes the form of a plurality of flared portions 325 separated by gaps such that these flared portions can be drawn inwardly radially together by engagement with the angled surface 323 of the collet housing 311 until the flared portions 325 come into contact with the wire 205.

Once the wire 205 has been clamped into position by rotation of the clamping screw 301, the wire 205 can be tensioned. Referring to FIG. 3D, the tensioning screw 303 includes distal threads 327 that are threadably engaged with corresponding threads 329 on an interior surface 331 of the housing 307. Rotation of the tensioning screw 303 causes the tensioning screw 303 to retract relative to the housing 307. The tensioning screw 303 is engaged with the clamping assembly 309 such that when the tensioning screw 303 is retracted relative to the housing 307, the clamping assembly 309 and the clamping screw 301 are also retracted. For example, a proximal surface 333 of the tensioning screw 303 can engage with a flange 335 of the clamping screw 301. The tensioning screw 303 can also be engaged with the clamping assembly 309 via internal threads (not shown). Accordingly, when the tensioning screw 303 is retracted from the housing 307, the proximal surface 333 of the tensioning screw contacts the flange 335 of the clamping screw 301, thereby causing the clamping screw 301 (and, correspondingly, the clamping assembly 309) to be retracted as well. As the clamping assembly 309 is clamped on the wire 205, retraction of the clamping assembly 309 increases tension in the wire 205.

In some embodiments, a spring 337 is disposed around the collet housing 311 between a distal flange 339 of the collet housing 311 and an engagement surface 341 of the interior surface 331. When compressed, this spring 337 urges the collet housing 311 (and, correspondingly, the clamping assembly 309) in a distal direction. This countervailing force provided by the spring 337 can provide for increased control in the amount of tension applied to the wire 205 during rotation of the tensioning screw 303.

FIGS. 4A-4C illustrate side cross-sectional views of a second tensioner clamp 211 in accordance with some embodiments. The second tensioner clamp 211 is engaged with the wire 209 during different points of operation of the second tensioner clamp 211. In particular, FIG. 4A illustrates the second tensioner clamp 211 prior to clamping the wire 209, FIG. 4B illustrates the second tensioner clamp 211 after clamping the wire 209, and FIG. 4C illustrates the second tensioner clamp 211 after clamping and tensioning the wire 209.

The second tensioner clamp 211 can utilize many features similar to the first tensioner clamp 207 described above with respect to FIGS. 3A-3D, for example by providing combined clamping and tensioning capabilities. However, the particular configuration of the tensioner clamp 211 utilizes alternative mechanisms to clamp and to tension the wire 209 can differ.

Referring to FIG. 4A, the second tensioner clamp 211 includes an outer housing 407 surrounding a clamping assembly 409. The outer housing 407 can be configured to be fixedly coupled to a ring of a ring fixator. The clamping assembly 409 includes a clamp body 411 with a central opening 413 that receives the wire 209 therethrough. A radial aperture 415 in the clamp body 411 is oriented transversely with respect to the central opening 413. For example, in some embodiments the aperture 415 can be perpendicular to the central opening 413. A clamping screw 417 (e.g., a set screw) can be threadably engaged with the aperture 415 and configured to be rotated to apply downward pressure onto the wire 209, as illustrated in FIG. 4B. Rotation of the clamping screw 417 into this position can clamp the wire 209 into position with respect to the clamping assembly 409.

Referring to FIG. 4C, the second tensioner clamp 211 includes a tensioning nut 419 that is threadably engaged with the clamp body 411 such that rotation of the tensioning nut 419 causes the clamp body 411 to be retracted with respect to the housing 407, thereby applying tension to the wire 209. In some embodiments, the second tensioner clamp 211 further includes a spring 421 surrounding a portion of the clamp body 411 and configured to urge the clamp body 411 away from the tensioning nut 419 when the clamp body 411 is retracted with respect to the housing 407. This countervailing force provided by the spring 421 can provide for increased control in the amount of tension applied to the wire 205.

In operation, a first driver (not shown) can be used to rotate the clamping screw 417, which causes is the clamping screw 417 to be downwardly threaded through the aperture 415 until it presses upon the wire 209 with sufficient pressure to clamp the wire 209 in place. A second driver (not shown) can then be used to rotate the tensioning nut 419, which causes tension to be applied to the wire 209. The tensioning nut 419 can be rotated to gradually increase and decrease the applied tension to the wire 209. The tensioning nut 419 can be rotated until the desired tension is applied to the wire 209. Rotation of the tensioning nut 419 in the opposite direction causes tension to be reduced on the wire 209. In other embodiments, a single driver can be used to control both the clamping screw 417 and the tensioning nut 419, thereby reducing the need for two separate drivers. In other embodiments, a single instrument can house a first driver for operating the clamping screw 417 and a second driver for operating the tensioning nut 419, thereby advantageously allowing a single instrument to perform both clamping and tensioning.

Often times, when attaching a ring fixator to a patient, one individual must hold a ring, while another extends the wires through the patient. Without an individual holding the ring, the ring fixator can slip and become disengaged during application. It has been found that providing a ring with a soft tissue spacer formed therein can help to retain the ring on the patient. The soft tissue spacer is advantageously designed to be removable such that once the ring of the ring fixator is put in place, it can be removed. By providing such a soft tissue spacer, this reduces the reliance on an individual having to hold the ring during installation of the ring fixator.

Figure 5:
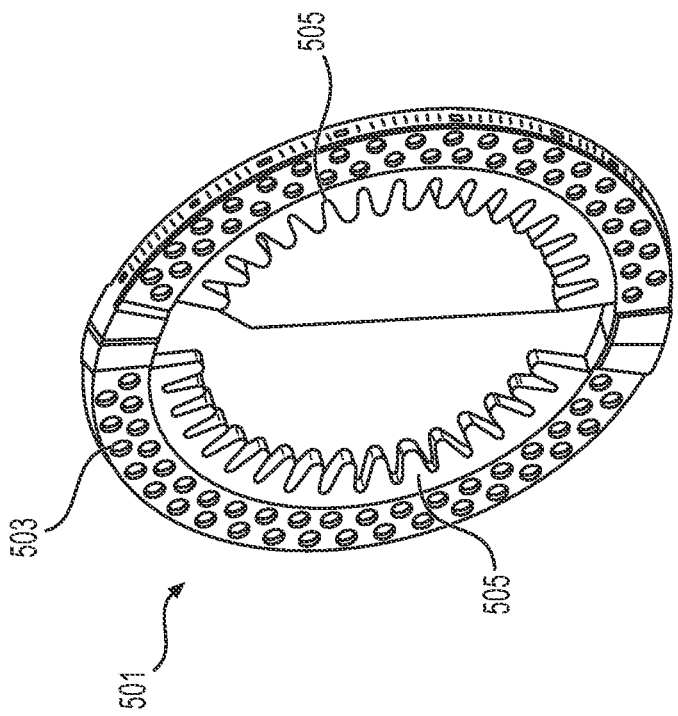
FIG. 5 illustrates a ring fixator with a soft tissue spacer in accordance with an embodiment of the present technology.

FIG. 5 illustrates a perspective view of a ring fixator 501 having a ring 503 and a spacer 505 coupled to the ring. The spacer 505 coupled to the ring can alleviate the need to rely on someone to hold the ring during installation. In some embodiments, the spacer 505 can be made of foam or other soft material, and can extend radially inwardly from the ring 503 so as to engage the anatomy of the patient. Providing a ring 503 with a soft tissue spacer 505 formed therein advantageously reduces the need to have an additional person hold the ring in place while applying the ring fixator. In addition, as the spacer 505 is formed of a soft material (e.g., foam), this provides added comfort to a patient during installation. The soft tissue spacer 505 can be removable such that once the ring fixator 501 is put in place, the spacer 505 can be removed. The soft tissue spacer 505 can be attached to the ring 503 via an adhesive or via nubs/protrusions that are insertable into openings in the ring. In some embodiments, the spacer 505 can be attached to the ring via an adhesive or via nubs/protrusions that are insertable into openings in the ring, thereby making it easy to attach and remove the spacer 505 from the ring.

As shown in FIG. 5, one or more spacers 505 can be attached to different segments of the inner wall of a ring. In the present embodiment, a first spacer is attached to one side of the ring, while a second spacer is attached to a second side of the ring. By providing a first spacer that is independent from a second spacer, this facilitates ease of attachment of the spacers within the ring. In addition, as shown in FIG. 5, each of the spacers can include recesses. These recesses can be in contact with the patient, and can advantageously help to accommodate varying patient anatomy.

Often times, a ring of a ring fixator (e.g., composed of two half circles) can be attached to a patient via bolts or screws. As the ring fixator is composed of multiple rings, it can be time consuming to perform the operation. It has been found that it is possible to reduce the time of the operation by providing various quick-connect mechanisms that allow a ring of a ring fixator to be attached to a patient quickly.

Figure 6:
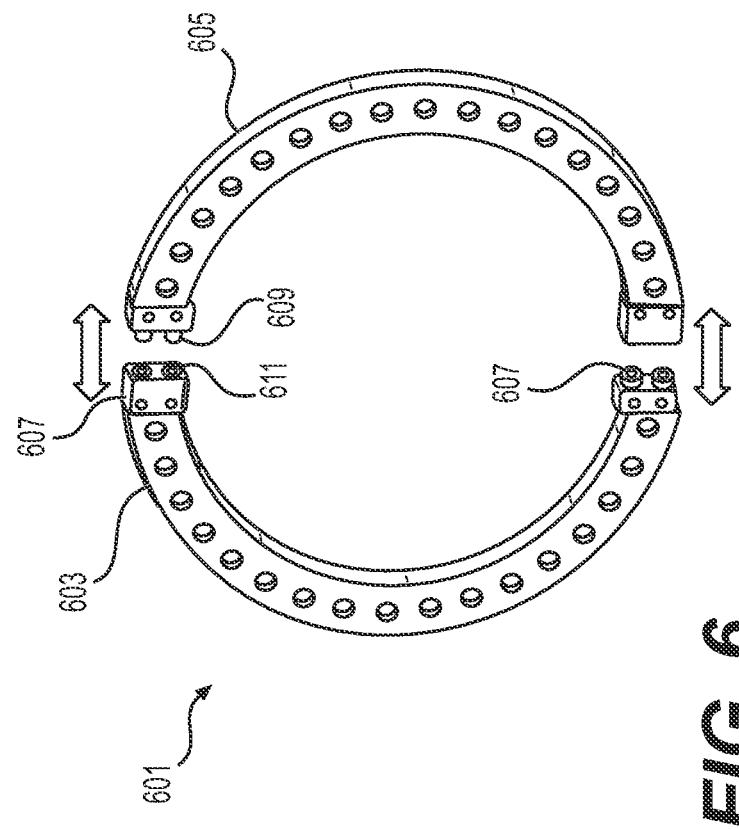
FIG. 6 illustrates a ring fixator with quick-connect segments in accordance with an embodiment of the present technology.

FIG. 6 illustrates a ring 601 having first and second members 603 and 605 joined by quick-connect components 607. The quick-connect components 607 shown in FIG. 6 advantageously allow the first and second members 603 and 605 to be secured together quickly. In the illustrated embodiment, the quick-connect components 607 include pins 609 and corresponding recesses 611 to receive the pins 609 therein. The quick-connect components 607 can take various other forms, such as mateable notches and protrusions, grooves and nubs, etc. In some embodiments, the quick-connect components 607 can include magnetic holding features in addition to or in lieu of mechanical mating features. In some embodiments, the two members 603 and 605 can be connected using these quick connect components 607 in addition to traditional screws, thereby forming a way to rapidly secure the two members 603 and 605 together while initially applying the ring fixator to a patient, while still allowing for a more robust fixation to be applied at a later stage through the use of screws.

Although many of the embodiments are described above with respect to devices, systems, and methods for ring fixators, other embodiments are within the scope of the present technology. Additionally, other embodiments of the present technology can have different configurations, components, and/or procedures than those described herein. For example, other embodiments can include additional elements and features beyond those described herein, or other embodiments may not include several of the elements and features shown and described herein. In particular, the ring fixators can be combined and used with other types of fixators, including rod fixators. In addition, the ring fixators can be used with various components used to heal bone fractures, including but not limited to, plates, rods, and screws.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the invention have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

I claim:

1. A method for stabilizing bone comprising the steps of: providing a ring fixator assembly comprising:
    a ring configured to surround a bone;
    at least one tensioner clamp disposed on the ring at a first position; and
    a wire disposed within the tensioner clamp and fixated to the ring at a second position,
    positioning the at least one tensioner clamp to clamp the wire by rotating a clamping member and provide tension to the wire by rotating a tensioning member.

2. The method of claim 1, wherein the clamping member and the tensioning member are configured to be controlled by a single driver.

3. The method of claim 1, wherein the tensioner clamp comprises a housing surrounding a clamping assembly, the clamping assembly comprising:
    a collet housing; and
    a collet received at least partially within the collet housing,
    wherein the wire passes through a central opening in the collet,
    wherein the clamping member comprises a clamping screw threadably engaged with the collet such that rotation of the clamping screw causes the collet to be drawn into the collet housing, thereby clamping the wire, and
    wherein the tensioning member is a tensioning screw that is configured to threadably engage with the housing and to couple to the clamping assembly.

4. The method of claim 3, wherein the collet comprises a compressible end portion that compresses when drawn into the collet housing, thereby clamping the wire.

5. The method of claim 3, wherein the tensioning screw is coaxial with the clamping screw.

6. The method of claim 1, wherein the tensioner clamp comprises a housing surrounding a clamping assembly, the clamping assembly comprising:
    a clamp body with a central opening that receives the wire therethrough; and
    an aperture in the clamp body, the aperture transverse to the central opening,
    wherein the clamping member is a set screw threadably received in the aperture such that rotation of the set screw applies pressure to the wire, thereby clamping the wire within the clamp body.

7. The method of claim 6, further comprising a spring within the housing and surrounding a portion of the clamp body, the spring configured to urge the clamp body away from the tensioning member.

8. The method of claim 1, wherein the ring comprises:
    a first ring portion;
    a second ring portion; and
    a quick-connect assembly that releasably couples the first ring portion to the second ring portion.

9. The method of claim 8, wherein the quick-connect assembly comprises first magnetic features disposed on ends of the first ring portion and second magnetic features disposed on ends of the second ring portion, the first and second magnetic features configured to be magnetically joined together.

10. A method for stabilizing bone comprising the steps of: providing a ring fixator assembly comprising:
    a ring configured to surround a bone;
    a spacer coupled to the ring and extending radially inwardly from the ring, the spacer configured to engage a patient's anatomy when the ring is positioned around a patient's limb;
    at least one tensioner clamp disposed on the ring at a first position; and
    a wire disposed within the tensioner clamp and fixed to the ring at a second position
    positioning the at least one tensioner clamp to clamp the wire by rotating a clamping member and provide tension to the wire by rotating a tensioning member.

11. The method of claim 10, wherein the at least one tensioner clamp comprises a central passage configured to receive a wire therein.

12. The method of claim 11, wherein the clamping member comprises a clamping screw and the tensioning member comprises a tensioning screw, and wherein the clamping screw and the tensioning screw are configured to be controlled by a single driver.

13. The method of claim 11, wherein the tensioner clamp comprises a housing surrounding a clamping assembly, the clamping assembly comprising:
    a collet housing; and
    a collet received at least partially within the collet housing,
    wherein the wire passes through a central opening in the collet,
    wherein the clamping member is configured to threadably engage with the collet such that rotation of the clamping member causes the collet to be drawn into the collet housing, thereby clamping the wire.

14. The method of claim 13, wherein the tensioning member is configured to threadably engage with the housing and couple to the clamping assembly.

15. The method assembly of claim 13, wherein the collet comprises a compressible end portion that compresses when drawn into the collet housing, thereby clamping the wire.

16. The method of claim 15, wherein the compressible end portion comprises flared portions separated by gaps.

17. The method of claim 13, wherein the tensioning member is coaxial with the clamping member.

18. The method of claim 11, wherein the tensioner clamp comprises a housing surrounding a clamping assembly, the clamping assembly comprising:
    a clamp body with a central opening that receives the wire therethrough; and
    an aperture in the clamp body, the aperture transverse to the central opening,
    wherein the clamping member is a set screw threadably received in the aperture such that rotation of the set screw applies pressure to the wire, thereby clamping the wire within the clamp body.

19. The method of claim 18, wherein the tensioning member comprises a tensioning nut threadably engaged with the clamping assembly and coupled to the housing.

20. The method of claim 19, further comprising a spring within the housing and surrounding a portion of the clamp body, the spring configured to urge the clamp body away from the tensioning nut.

* * * * *